(12) United States Patent
Blumhofer et al.

(10) Patent No.: US 6,865,253 B2
(45) Date of Patent: Mar. 8, 2005

(54) METHOD AND DEVICE FOR ACCURATELY POSITIONING A PATIENT IN RADIOTHERAPY AND/OR RADIOSURGERY

(75) Inventors: Andreas Blumhofer, München (DE); Stephan Fröhlich, Aschheim (DE); Rainer Lachner, Poing-Angelbrechting (DE); Cornel Schlossbauer, Aschheim (DE)

(73) Assignee: BrainLAB AG, Kirchheim/Heimstetten (DE)

( * ) Notice: Subject to any disclaimer, the term of this patent is extended or adjusted under 35 U.S.C. 154(b) by 194 days.

(21) Appl. No.: 09/955,470

(22) Filed: Sep. 18, 2001

(65) Prior Publication Data
US 2002/0085668 A1 Jul. 4, 2002

(30) Foreign Application Priority Data
Oct. 17, 2000 (DE) .......................................... 100 51 370

(51) Int. Cl.[7] .............................................. A61N 5/10
(52) U.S. Cl. .......................................... 378/65; 378/205
(58) Field of Search ................................ 378/63, 10, 9, 378/205, 98.12, 165, 65, 197, 92, 21, 68, 64; 604/20; 607/1

(56) References Cited

U.S. PATENT DOCUMENTS

| | | |
|---|---|---|
| 4,118,631 A | 10/1978 | Froggatt |
| 4,233,519 A | 11/1980 | Coad |
| 4,633,494 A | 12/1986 | Klausz |
| 4,791,934 A | 12/1988 | Brunnett |
| 4,846,173 A | 7/1989 | Davidson |
| 4,868,843 A | 9/1989 | Nunan |
| 5,127,032 A | 6/1992 | Lam et al. |
| 5,205,289 A | 4/1993 | Hardy et al. |
| 5,207,223 A | 5/1993 | Adler |
| 5,315,630 A * | 5/1994 | Sturm et al. .................. 378/65 |
| 5,373,844 A | 12/1994 | Smith et al. |
| 5,427,097 A | 6/1995 | Depp |
| 5,430,308 A | 7/1995 | Feichtner et al. |
| 5,446,548 A | 8/1995 | Gerig et al. |

(List continued on next page.)

FOREIGN PATENT DOCUMENTS

WO         02/22019         3/2002

*Primary Examiner*—Edward J. Glick
*Assistant Examiner*—Hoon Song
(74) *Attorney, Agent, or Firm*—Renner, Otto, Boisselle & Sklar, LLP

(57) ABSTRACT

A method for accurately positioning a patient for radiotherapy and/or radiosurgery, comprising the following steps: the patient is pre-positioned as accurately as possible with respect to a linear accelerator; at least two x-ray images of the patient and/or one of the parts of his body in the vicinity of the radiation target point are produced from different respective recording angles on a single image recorder; the x-ray image is spatially localized; at least one reconstructed image, corresponding to each x-ray image and deriving from a three-dimensional patient scan data set, is produced, the reconstructed images containing the desired image contents of the x-ray images when the patient is correctly positioned; and the real x-ray images are superimposed, and the positioning error is determined electronically and/or with computer guidance by way of particular landmarks and/or the intensity gradient or the contours in the two images; and the position of the patient is corrected by way of the determined positioning error.

23 Claims, 6 Drawing Sheets

U.S. PATENT DOCUMENTS

| | | |
|---|---|---|
| 5,537,452 A | 7/1996 | Shepherd et al. |
| 5,588,430 A | 12/1996 | Bova et al. |
| 5,695,501 A | 12/1997 | Carol et al. |
| 5,727,554 A | 3/1998 | Kalend et al. |
| 5,748,700 A | 5/1998 | Shepherd et al. |
| 5,800,353 A | 9/1998 | McLaurin, Jr. |
| 5,815,547 A | 9/1998 | Shepherd et al. |
| 5,894,503 A | 4/1999 | Shepherd et al. |
| 5,899,857 A | 5/1999 | Wilk |
| 6,076,005 A | 6/2000 | Sontag et al. |
| 6,113,264 A * | 9/2000 | Watanabe ................... 378/197 |
| 6,118,848 A | 9/2000 | Reiffel |
| 6,125,164 A * | 9/2000 | Murphy et al. ............... 378/65 |
| 6,144,875 A | 11/2000 | Schweikard et al. |
| 6,314,312 B1 | 11/2001 | Wessels et al. |
| 6,422,748 B1 | 7/2002 | Shepherd et al. |
| 6,454,776 B1 | 9/2002 | Tajima et al. |
| 6,501,981 B1 | 12/2002 | Schweikard et al. |

* cited by examiner

METHOD AND DEVICE FOR ACCURATELY POSITIONING A PATIENT IN RADIOTHERAPY AND/OR RADIOSURGERY

BACKGROUND

Great progress has been made in radiotherapy and radiosurgery recently in dosage planning. People are striving to move treatment more and more in the direction of radiosurgery, i.e. working with high radiation dosages applied in a few, and preferably in just a single, radiation treatment to a target volume, so for example to a tumour. Although dosage planning is, as mentioned, relatively successful, the use of high doses administered in a few or a single fraction is often obstructed by the fact that the patient and/or the body section to be irradiated can be positioned only relatively imprecisely. In order to avoid significant damage to healthy tissue, one therefore falls back in most cases on conventional fractionated radiotherapy, in which repeated irradiation with small doses is applied.

In order to improve positioning, one is currently still making do with a very imprecise "manual" method, whereby an x-ray image of a body section of the patient is produced on the linear accelerator. This image is compared with a reference x-ray image previously taken on the simulator (an x-ray device with an identical geometry to the linear accelerator). The doctor carrying out the treatment then compares the x-ray image and the simulator image, for example on a viewing box, thereby determining the positioning error between the actual position of the patient and the desired position using a ruler and then shifting the patient accordingly. At best, a centre-beam cross and/or the contour of the outer field boundary in both images are also available to the doctor as a starting point. The field boundaries may be defined by lead blocks or mobile radiation screens, respectively. Even when comparing with DRRs ("simulator images" virtually determined from a three-dimensional image data set) instead of with actual simulator images, this method does not change.

Disadvantageously, this way of positioning the patient is imprecise, for the following reasons alone:

The images are projective, and therefore not to original scale. (No uniform image scale exists).

The "manual" reading of the required shift is imprecise.

A three-dimensional spatial shift from two-dimensional images and without computer assistance is only possible to a limited extent, and requires a very experienced user.

An iterative method for aligning therapy radiation with a treatment target is known from U.S. Pat. No. 5,901,199, wherein diagnostic computer tomography data are used, with the aid of which a multitude of reconstructed x-ray images, so-called DRRs (Digitally Reconstructed Radiographs), are generated. These DRRs are repeatedly produced and compared with a x-ray image taken at the source, until one is found which shows a sufficient correspondence. With the aid of the data thus obtained, the position of the treatment device and/or of the beam used for treatment is corrected such that the beam hits the treatment target.

A disadvantage of this method is the high computational demands, since such DRRs initially have to be generated at random, and a great many DRRs have to be compared with the actual x-ray image. In particular, an "intelligent" algorithm needs to be found in order to approach the matching DRR for each body section and for each patient in turn in a reasonable period of time.

Furthermore, a method is known in principle for producing x-ray images at the source in a treatment room, in order to integrate the up-to-date information thus gained about the position of the treatment target and its surroundings into the course of the treatment, whereby two securely assembled x-ray sources are regularly used laterally above the patient in radiation treatment, as well as two securely installed image recorders, e.g. let into the floor of the treatment room, with a separate image recorder for each x-ray source. These systems are inflexible and costly in terms of apparatus, and therefore also expensive.

SUMMARY OF THE INVENTION

It is the object of the present invention to propose a method and a device for accurately positioning a patient for radiotherapy and/or radiosurgery, wherein the above disadvantages of the prior art are not present. In particular, a greater flexibility in producing images and a cost-effective system are to be made available.

This object is solved in accordance with the invention by a method for accurately positioning a patient for radiotherapy and/or radiosurgery, comprising the following steps:

a) the patient is pre-positioned as accurately as possible with respect to a linear accelerator;
b) at least two x-ray images of the patient and/or one of the parts of his body in the vicinity of the radiation target point are produced from different respective recording angles on a single image recorder;
c) the x-ray image is spatially localised;
d) at least one reconstructed image, corresponding to each x-ray image, especially isocentrically, and deriving from a three-dimensional patient scan data set, is produced;
e) the reconstructed image and the x-ray images are superimposed, and the positioning error is determined electronically and/or with computer guidance by way of particular landmarks, the intensity gradient or the contours in the two images; and
f) the position of the patient is corrected by way of the determined positioning error.

The advantageous nature of the present invention is based, among other things, upon the fact that the x-ray images are produced on a single image recorder. Through this, the overall construction is naturally more cost-effective, and gains above all in flexibility, because a single image recorder can much more easily be placed right where it is most effective. In particular, it can also be provided mobile, which opens additional possibilities in recording technology for the overall method.

Furthermore, repositioning as proposed in accordance with the invention offers a very quick and simple way of achieving very accurate target irradiation. Determining the positioning error electronically and/or with computer guidance considerably increases accuracy as compared to manual methods. Spatially localising the x-ray image allows even this input value to be evaluated with sufficient accuracy, such that errors and delays in repositioning may also be avoided from this side.

In a preferred embodiment of the method in accordance with the invention, the x-ray images are produced in positions defined offset with respect to the pre-positioning, outside of the radiation range of the linear accelerator, the reconstructed images being produced with the same offset. Positioning of the image recorder for the x-ray images absolutely outside the primary beam of the linear accelerator can thus be achieved. While correcting the position of the patient, the defined offset is then compensated for, together with the positioning error.

Within the framework of the method in accordance with the invention, there exists the possibility of producing the x-ray images at an oblique angle on an image recorder spatially arranged horizontally, and of projecting them back onto each respectively defined normal plane, the corresponding reconstructed images being likewise produced in these normal planes. Such images in the normal plane do not suffer from distortions, and are therefore easier to interpret visually.

In a method in accordance with the invention, the patient is pre-positioned by means of a navigation and tracking system with computer and camera guidance, with the aid of artificial, in particular reflecting, arrangements of markers on the patient and on the devices for treatment. In carrying out the method in accordance with the invention, such a navigation and tracking system can assume all necessary position determination and output corresponding information, for example to a computer display unit.

The patient can, however, also be pre-positioned using markings on the patient's skin, natural landmarks or laser markings.

The x-ray images and the reconstructed images can in accordance with the invention be superimposed by way of natural structures present in the x-ray images and the reconstructed images, in particular bone structures. On the other hand, or in combination therewith, the x-ray images and the reconstructed images can be superimposed by way of artificial structures present in the x-ray images and the reconstructed images, in particular by way of implanted markers, preferably gold spheres.

In an embodiment of the method in accordance with the invention, the x-ray images and the reconstructed images are superimposed by marking and sliding over one another on a computer display unit by the operator (e.g. using a mouse, keyboard, touch screen, joystick, etc.). On the other hand, the x-ray images and the reconstructed images can also be superimposed by automatic, computer-guided image fusion.

In preferred embodiments of the method in accordance with the invention, the reconstructed image/s is/are produced as:

Digitally Reconstructed Radiographs (DRRs);
Digitally Composited Radiographs (DCRs);
MIP images.

or as any two-dimensional image reconstruction from a three-dimensional patient scan data set.

The position of the patient can be altered by shifting the patient table, in particular while correcting the positioning error, but also during any other alterations to the position, and in particular can be automatically guided and corrected by a navigation and tracking system with computer and camera guidance, using markers on the patient and on the patient table. Naturally, the position of the patient may also be corrected by manually guiding the table.

In accordance with an advantageous embodiment of the method in accordance with the invention, a multitude of images over a breathing cycle are produced from each angle, each time x-ray image are produced from the different recording angles, the breath-dependent movement of the markings arranged on the patient or in the vicinity of the radiation target being tracked by a navigation and tracking system with computer and camera guidance and referenced with the dynamic shifting of the target point directly or indirectly (e.g. via implanted markers) visible in the images. The breath-dependent movement of the radiation target is reckoned back, in order to enable breath compensation during irradiation.

The invention further relates to a device for accurately positioning a patient for radiotherapy and/or radiosurgery, comprising:

a) at least two x-ray sources with which x-ray images of the patient and/or one of the parts of his body in the vicinity of the radiation target point may be produced from different recording angles;
b) a means by which the x-ray image may be spatially localised;
c) a means by which at least one reconstructed image, corresponding to each x-ray image and deriving from a three-dimensional patient scan data set, may be produced;
d) a means by which the reconstructed image and the x-ray images are superimposed, the positioning error being determined electronically and/or with computer guidance by way of particular landmarks and/or the intensity gradient or the contours in the two images; and
e) a means by which the position of the patient is corrected with respect to a linear accelerator by way of the determined positioning error, wherein
f) the device comprises only one image recorder, with which the x-ray images of both x-ray sources are produced.

The advantages of using a single image recorder have already been described above. The image recorder can be an image intensifier or detector, in particular comprising amorphous silicon.

In a preferred embodiment of the present invention, the image recorder is positioned on a support for a movable patient table. In this way, one or more image recorders rigidly installed in the floor of the treatment room may be dispensed with, resulting in very high flexibility. The treatment room can then easily be used for other purposes as well, without disruptive image recorders in the floor. Moreover, an image recorder positioned on a support for a movable patient table is much more easily accessible, and can therefore also be more easily serviced. The image recorder may be vertically portable together with the patient table and the support, while it is securely arranged horizontally. In other words, the patient table may be moved horizontally, independent of the image detector. If the two x-ray sources are then arranged respectively over a patient table, in particular fixed to the ceiling, and to the side, shifting the patient table sideways while the image recorder remains secured in this direction may be used to ensure that even when the radiation target is on the patient's side, an image of the radiation target always appears on the image intensifier, and in a substantially central position in the image recorder.

In principle, however, the possibility also exists of arranging the two x-ray sources respectively beneath a patient table, and to the side, the image recorder then being positioned above the patient table.

BRIEF DESCRIPTION OF THE DRAWINGS

In the following, the invention will be explained in more detail, by way of the enclosed drawings showing preferred embodiments, in which.

DETAILED DESCRIPTION

Referring to the figures mentioned above, those components of the device in accordance with the invention will now be described which are necessary for carrying out the preferred embodiment of the invention described here. The device comprises two x-ray tubes 2, 3 mounted to the ceiling of a radiotherapy room, which in other embodiments may also optionally be fixed in or on the floor.

Furthermore, an x-ray detector 6 (image recorder) made of amorphous silicon is provided, fixed to a support 5 for a patient table 4. The x-ray detector can be moved vertically using the support 5, the patient table 4 can however be moved horizontally, independent of the detector 6. In other embodiments, the detector can consist of another material, or can be an image intensifier; it can also be fixed to the floor or to the ceiling, according to the location of the x-ray tubes.

Figure 3:
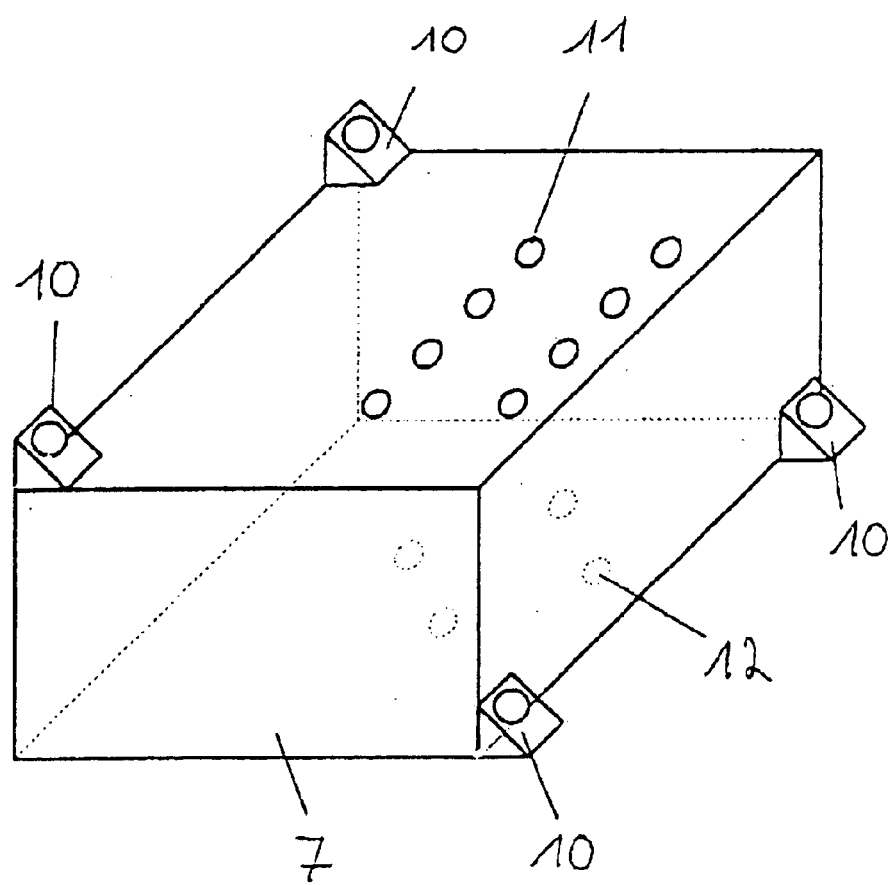
FIG. 3 is a calibration phantom.
Figure 4:
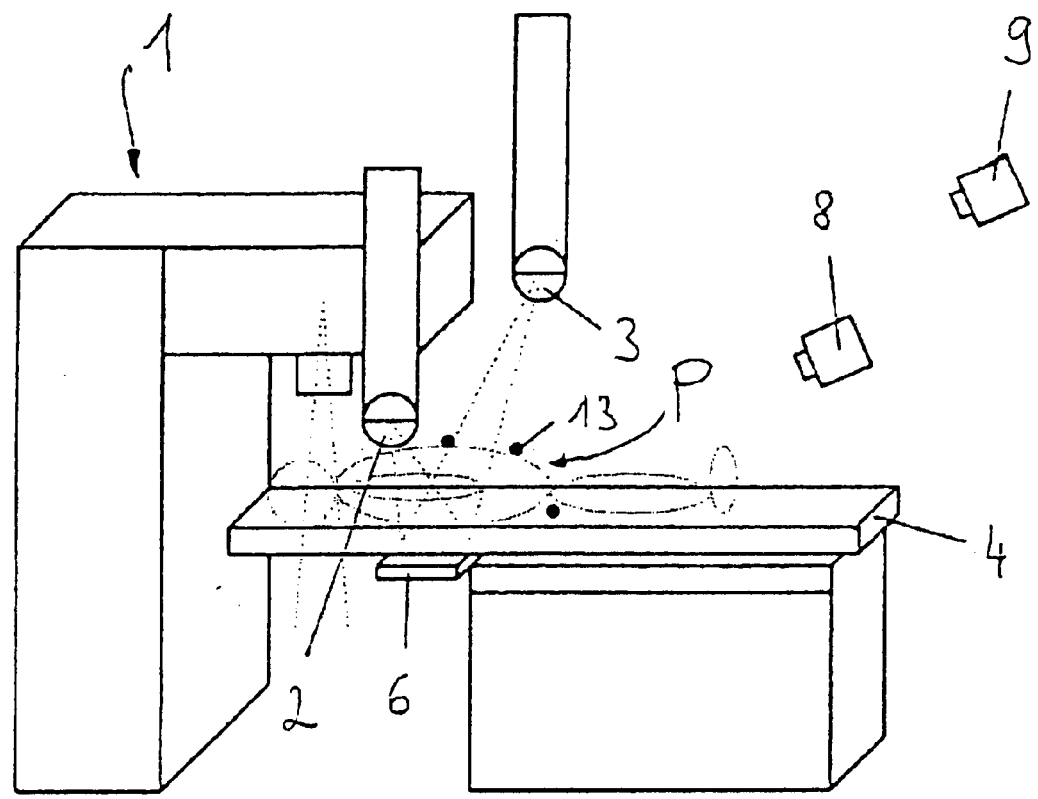
FIG. 4 is the radiation device, as x-ray images of a patient are being produced.
Figure 7:
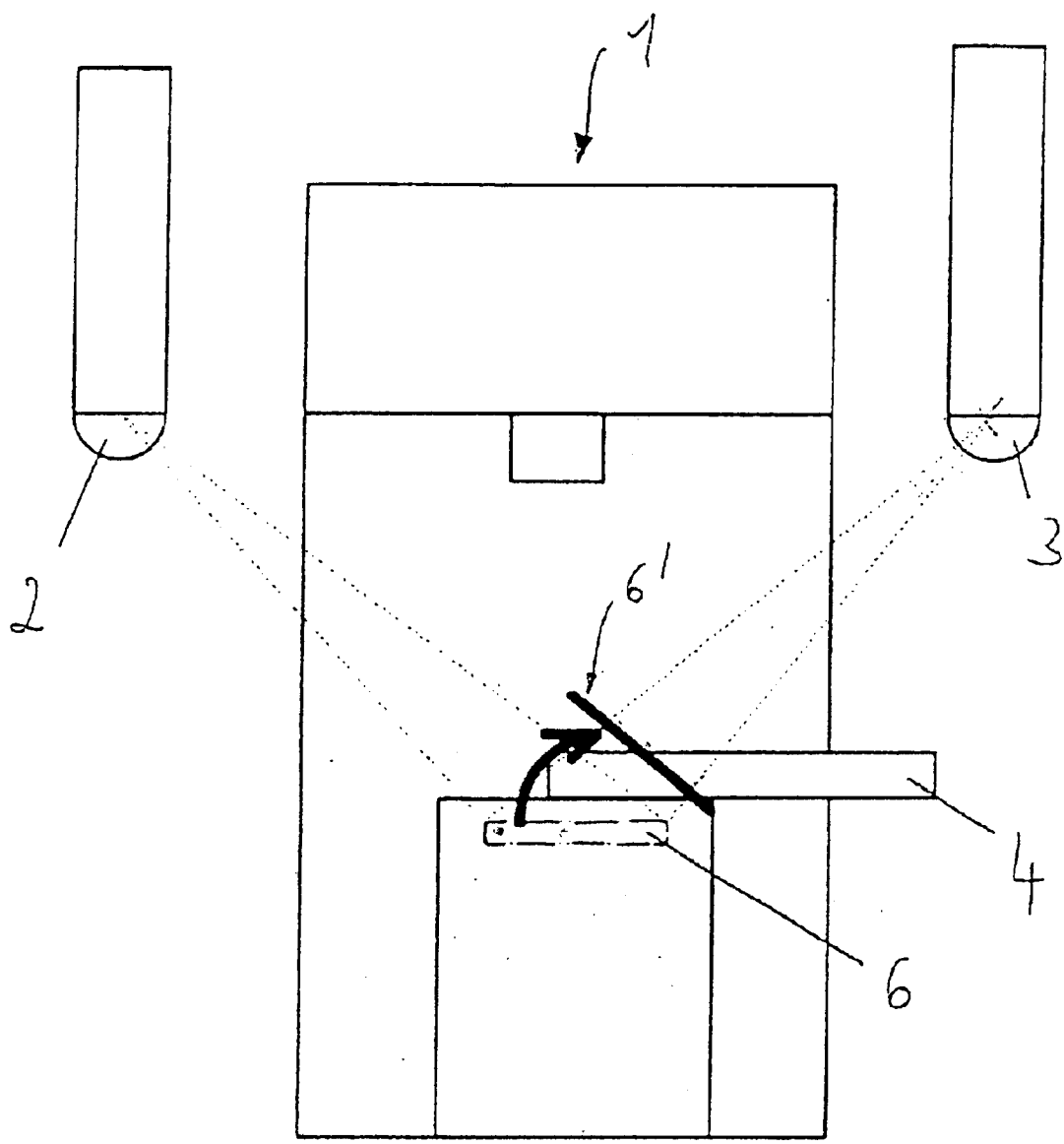
FIG. 7 is the scheme for projecting an x-ray image back into a normal plane.

The device further includes an infrared tracking system with cameras 8, 9 for tracking passive markers 10, 13 (FIG. 3 and FIG. 7), wherein in principle any tracking system for tracking markers or contours can conceivably be used. The computer system for guiding the tracking system, the x-ray sources 2, 3, the detector 6 and optionally the patient table and in particular the gantry of the linear accelerator 1 is present, but not shown in the drawings.

Furthermore, an x-ray calibration phantom 7 is available, comprising both x-ray visible markings 11, 12 on a number of planes as well as markings 10 which may be detected by the tracking system. Optionally, the position of the phantom may also be communicated to the system via the position of the patient table 4 and a phantom placed defined on the table 4.

Additionally, the system may comprise an isocentre phantom, not shown, with the aid of which, and including the tracking system, the spatial position of the isocentre of the linear accelerator may be communicated to the computer system.

In an alternative embodiment, all positions detected by the tracking system may also be read from a patient table comprising an integrated (electronic) position indicator. Conversely, positions determined without a tracking system can therefore also be approached, wherein the x-ray calibration phantom 7 then has to lie exactly on a defined marking during calibration. Moreover, a determining means should also be provided for the patient, for example rubber tensors or a vacuum means.

The invention will be explained in the following by way of an extended positioning sequence, and referring to all figures for an example embodiment. In preparation, a three-dimensional image data set (for example, a series of computer tomographic images) are taken for a patient, taking care that the region to be irradiated is captured. This image data set is transferred to a radiation planning system. The desired position of the radiation target point is defined with the aid of the radiation planning system (later, during irradiation, the radiation target point defined in this way should lie in the focus of the beam of the linear accelerator (=the isocentre)). Image information, and radiation target point information referenced thereto, are transferred to the positioning system, wherein it should optionally be possible to define a number of target points which are then processed sequentially.

A calibration step for the device now follows. This calibration step need not be carried out before every treatment, but only when it is suspected that the relative position of the x-ray sources has changed.

When calibrating, the calibration phantom 7 is first placed directly onto the detector 6. The spatial position of the phantom 7 is determined via the tracking system and the tracking markers 10 arranged on the phantom 7. Then, without moving the phantom, two x-ray images are taken, which may be seen in FIG. 2 (one image per x-ray source), and read into the computer system. The projections of all x-ray visible markers in both x-ray images are then automatically detected in the computer system with the aid of image processing software; detection may also optionally take place manually.

From the position of the phantom and the projections of the positions of the x-ray visible markers, the computer system calculates the three-dimensional spatial position of the x-ray sources (the focus of the beam), the three-dimensional position of the detector (the image plane) during calibration, as well as other indexing parameters. The spatial position of the isocentre of the linear accelerator is disclosed to the computer system with the aid of another phantom, as has already been described above.

The patient can now be accurately positioned in accordance with the present invention. To this end, the patient P is placed on the patient table 4 and initially pre-positioned in the treatment position as accurately as possible with respect to the linear accelerator 1. The patient may be pre-positioned via the tracking system using the markers 13 arranged on the patient; or, however, manually or by means of a different method.

Figure 5:
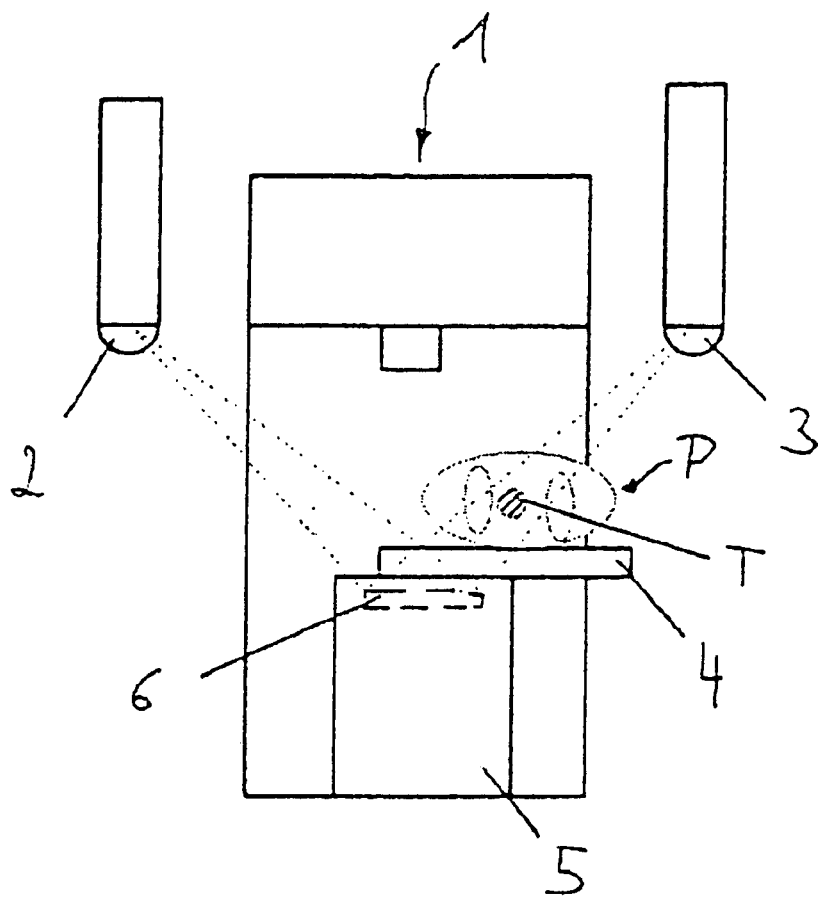
FIGS. 5 & 6 are the production of x-ray images of a patient in two different recording positions.

In the next step, the patient P is moved back out of pre-positioning using a defined offset, and into a recording position I, as shown in FIG. 5. Recording position I is characterised by the fact that the region to be irradiated is projected onto the detector 6 using the x-ray source 3. The patient can then be shifted by directly guiding the patient table 4 with the aid of co-ordinates and guiding the patient table 4 with the aid of the tracking system and markers 13 arranged on the patient P or on the table 4. Furthermore, the patient may also be manually shifted. As already noted previously, recording position I lies outside the radiation range of the linear accelerator 1, and the shifting of the patient with respect to pre-positioning is stored as "offset I". An x-ray image (x-ray image—actual position I) is now taken with the aid of the x-ray source 3 and the detector 6, and transferred to the computer system.

The spatial position of the image detector 6 while "x-ray image—actual position I" is being taken is determined. This may be achieved by detecting edges in the x-ray image using known setting and form of the diaphragm of the x-ray source. Optionally, the position of the detector determined during calibration may be enlisted, to calculate the current position of the detector, if the detector is only moved vertically. Furthermore, it is also possible to track markings 10 arranged on the detector 6, with the aid of the tracking system.

Figure 6:
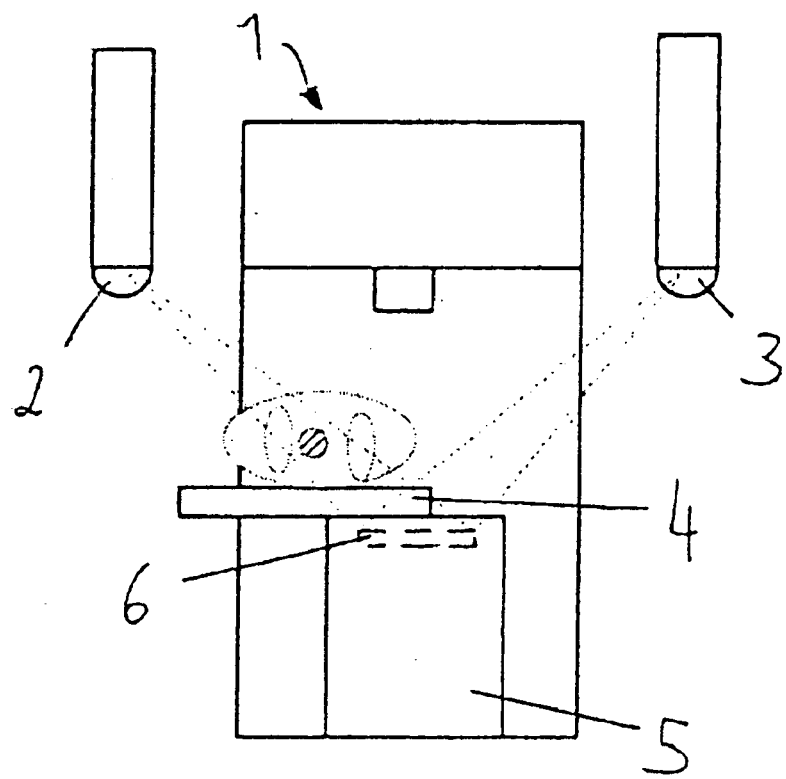

In a further step, the patient P is now moved into recording position 11, shown in FIG. 6. Recording position 11 is characterised by the fact that the region to be irradiated, the radiation target point T, is projected onto the detector 6 using the x-ray source 2. Here too, the patient can then be shifted by the measures already mentioned above. Recording position II also lies outside the radiation range of the linear accelerator 1, and the shifting of the patient with respect to recording position I is stored as "offset II".

An x-ray image ("x-ray image—actual position II") is then produced with the aid of the x-ray source 2 and recorded by the x-ray detector 6, and transferred to the computer system.

At this point, too, the spatial position of the image detector 6 is determined by the measures already cited previously.

Figure 1:
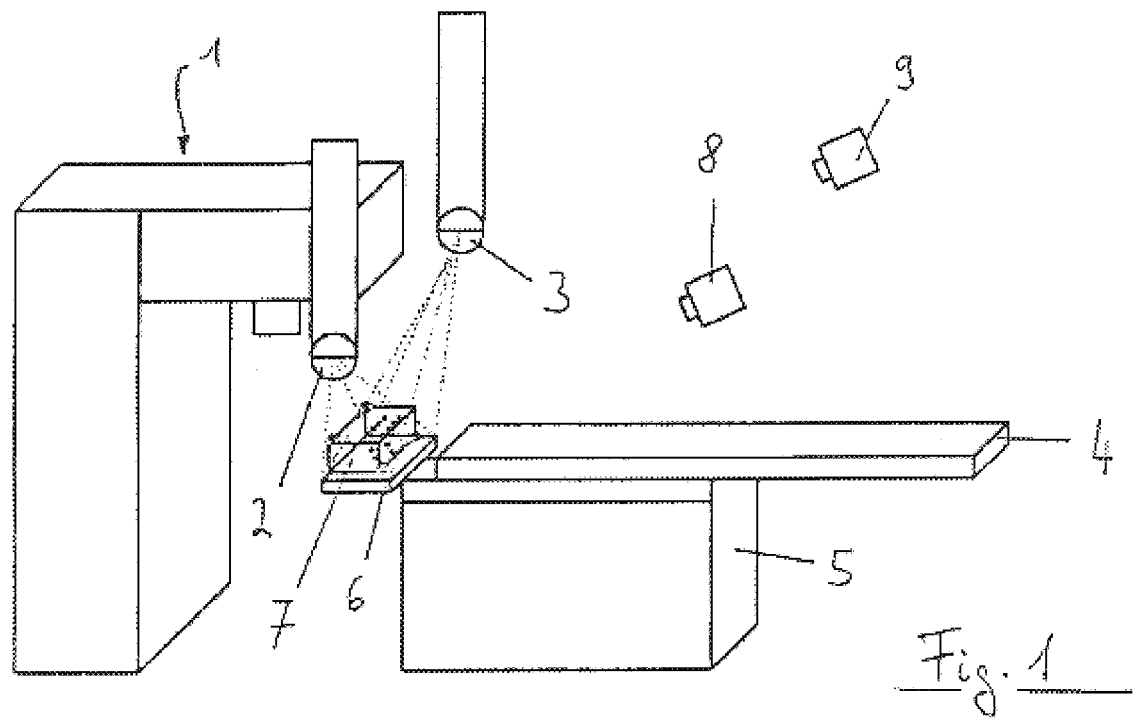
FIG. 1 is a radiation device in accordance with the invention, during a calibration process.
Figure 2:
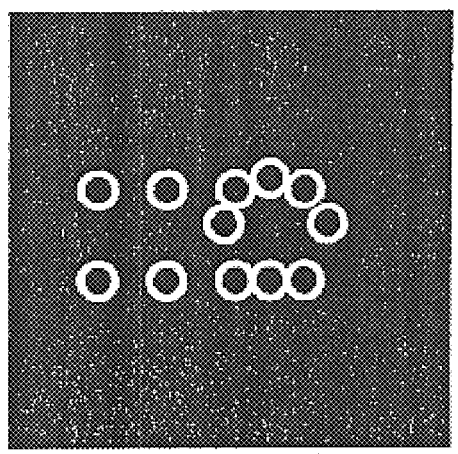
FIG. 2 is two images of a calibration phantom (x-ray images of a calibration phantom)
Figure 2:
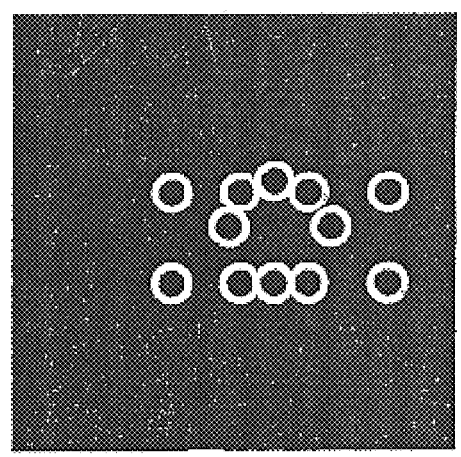
Figure 8:
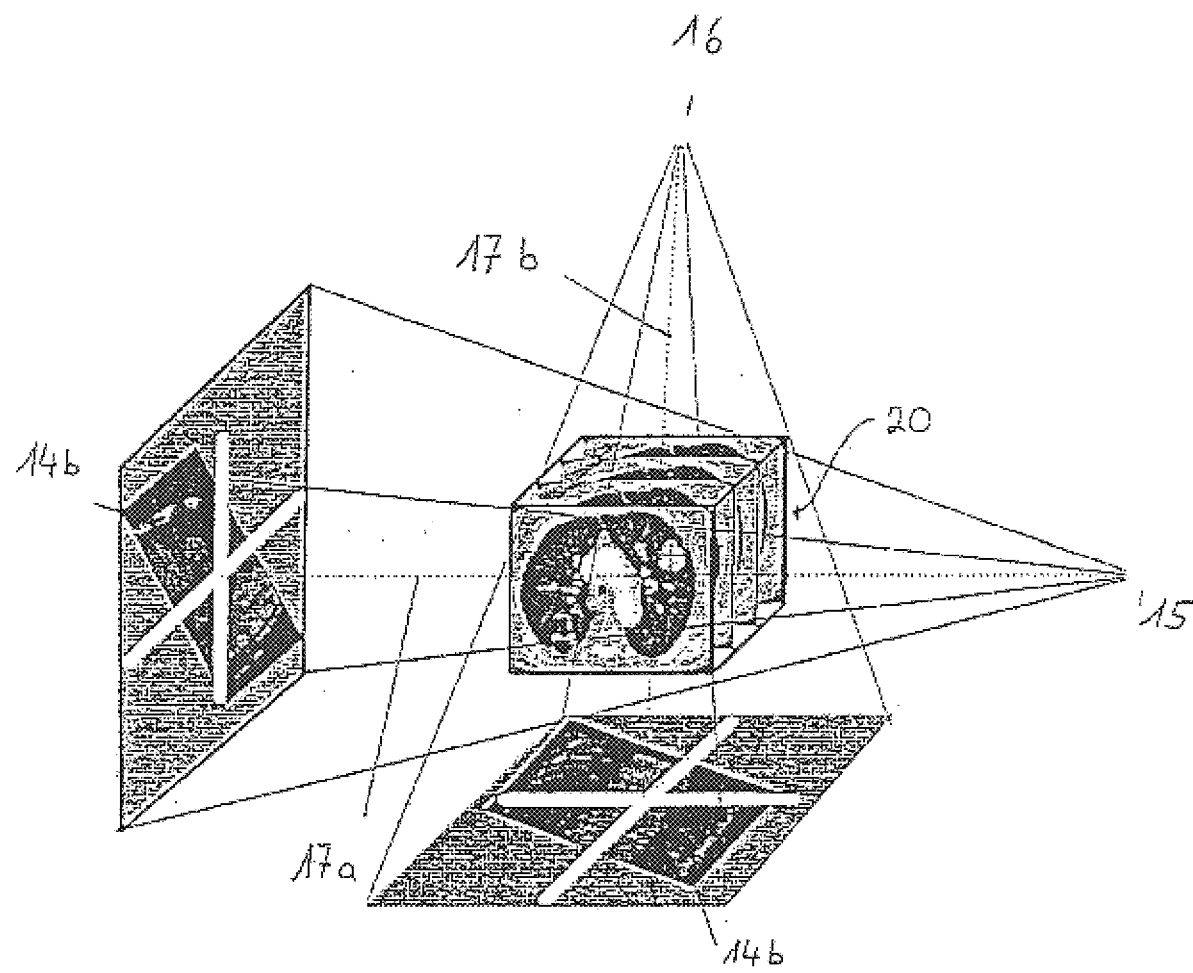
FIG. 8 is a schematic representation of the production of two reconstructed images.

Following this, the reconstructed images or virtual images (DRRs=Digitally Reconstructed Radiographs) corresponding to the x-ray images are then produced. FIG. 8 schematically explains how two reconstructed images are produced. To this end, a computer tomographic scan data set 20 is used which was produced previously from the patient. It is illustrated in FIG. 8 by a multitude of cross-sectional views arranged in sequence. Using the known position data of the radiation sources 2 and 3, which correspond here to the virtual radiation sources 16 and 15, corresponding reconstructed images 14a and 14b are then generated by way of the data scanned in. In FIG. 2, the centre-beams are designated 17a and 17b.

The input data for producing the reconstructed images, which in the following are also called DRRs (Digitally Reconstructed Radiographs), are on the one hand the positions of the radiation sources 15 and 16. The spatial arrangement of the plane in which the x-ray image is produced, both with respect to the distance to the radiation source as well as with respect to its inclination, must be given as the second input quantity. In other words, the virtual x-ray films 14a and 14b must be arranged in exactly the same way as the films or surface of the detector from the actual x-ray images, in order that the images may be superimposed. If the x-ray image plane and the direction of the centre-beam are exactly known (these parameters are determined as described previously), the corresponding DRRs can be exactly reconstructed and assigned.

In this way, virtual x-ray images (DRRs) defining the "desired content" of the real x-ray images are calculated analogously to the really existing x-ray images "actual position I" and "actual position II" by the computer system with the aid of three-dimensional image data set. The procedure is as follows, wherein all steps are carried out virtually and completely by the software of the computer system:

The three-dimensional image data set is positioned "correctly" in virtual space. In this case, this means that the defined radiation target point is exactly on the isocentre position known to the computer, and is correctly orientated. The image data set is then shifted virtually in the direction of the real "x-ray image—actual position I" using "offset I".

The x-ray source 3 and the detector 6 are virtually arranged spatially correctly, i.e. in the previously determined three-dimensional positions. In this case, spatially correctly means that the system parameters determined during calibration are used, with the exception of the position of the detector The position determined while "x-ray image—actual position I" is taken is considered as the position of the detector.

The "desired x-ray image—DRR I" is generated by virtually transilluminating the three-dimensional image data set (taking into account the size of the detector and the scaling of the data set). "Desired x-ray image—DRR I" and "x-ray image—actual position I" are thus of equal size; "desired x-ray image—DRR I", however, does not contain aperture shadows.

The data set is then virtually shifted in the direction of the real "x-ray image—actual position II" using "offset II".

Here, too, the x-ray source 2 and the detector are virtually arranged spatially correctly, i.e. in the previously determined three-dimensional positions, which in this case means that the system parameters determined during calibration are used, with the exception of the position of the detector. The position determined while "x-ray image—actual position II" is taken is considered as the position of the detector.

The "desired x-ray image—DRR II" is also generated by virtually transilluminating the three-dimensional image data set, taking into account the size of the detector and the scaling of the data set, such that "desired x-ray image—DRR II" and "x-ray image—actual position II" are of equal size, the former containing no aperture shadows.

"X-ray image—actual position I" is then superimposed with "desired x-ray image—DRR I", and "x-ray image—actual position II" with "desired x-ray image—DRR II", the DRR in each case having already been virtually generated spatially correctly on the x-ray image. The respectively assigned images are then compared, in that the image contents are manually or automatically superimposed. In this embodiment, "image contents" primarily means projections of bone structures. In this case, the shadows of the aperture remain explicitly unconsidered in the x-ray images. The automatic "superimposing" is based on an image fusing algorithm, which may be based on intensity marks, contour marks, or landmarks.

The necessary shifting of each of the "actual position" images is outputted and automatically converted to the real position of the patient. The three-dimensional dependence of the two-dimensional image pairs is likewise taken into account, i.e. shifting "x-ray image—actual position I" in the head-foot direction automatically leads to the same shifting in "x-ray image—actual position II". The three-dimensional shifting detected in this way will be called "positioning error compensation" in the following. Where both image pairs are already 100% congruent without having been shifted, the original pre-positioning was absolutely correct and the positioning error in all spatial directions was thus zero.

The patient is then moved into the correct position for treatment, by means of the tracking system, manually or by another method of shifting the patient table. This position for treatment is defined as follows:

position for treatment=current position−offset II−offset I+positioning error compensation An alternative to producing the x-ray images as outlined above is to project each of "x-ray image—actual position I" and "x-ray image—actual position II" back onto a defined normal plane. This projecting back, which may be performed computationally, is shown schematically in FIG. 7, wherein the image plane 6' inclined out from the real plane of the detector 6 is intended for radiation using the x-ray source 3. The corresponding DRRs are likewise calculated in these planes, cf. in this respect FIG. 8.

An alternative method for calculating the positioning error is based on using implanted markers, wherein an identical method to that described above is carried out, but with the following differences:

the positioning principle is not based on bone structures, but on markers (e.g. 2 mm gold spheres) already implanted in the patient before the 3D-image data set is recorded;

the position of the implants is detected in "x-ray image—actual position I" and "x-ray image—actual position II" (manually, or automatically by image processing software);

the position of the implants is detected in the 3D-image data set (manually, or automatically on the basis of density). Desired x-ray images DRR I and DRR II, calculated thereupon, explicitly contain the projected positions of the markers. Projecting bones and soft tissues may be dropped.

the positions of the markers alone are then superimposed, and a potential shift is calculated therefrom. In the case of negligible distortions, a compromise is optimised.

Lastly, the positioning system in accordance with the invention can be extended further, by taking into account the breath-dependence the positions of the radiation targets. Irradiation dependent on or triggered by breathing may be achieved by the following measures:

not one single image but a quick succession of a number of images (a video clip) are recorded in image recording positions I and II over a period of several breathing cycles;

one or more marker arranged on the patient (preferably on the chest) are tracked by the tracking system. These markers move in accordance with breathing. Each time an image is taken by the x-ray unit, the corresponding position of the markers is stored as well;

under certain circumstances, the breath-dependent movement of the target volume may be observed in the video clips. Preferably, however, markers implanted in the target volume or in the vicinity of the target volume are tracked, always being clearly recognisable in the x-ray images;

by this method, the movement of internal structures may be referenced with the movement of external markers. If the two video clips from recording position I and recording position II are aligned with one another via the external markers, the 3D position of an internal structure may be concluded from the current position of the external markers;

this may, for example, be used to activate the beam of the radiation device only when the target volume is within the radiation beam.

What is claimed is:

1. A method for accurately positioning a patient for radiotherapy and/or radiosurgery, comprising the following steps:
    a) the patient is pre-positioned with respect to a linear accelerator;
    b) after the patient has been pre-positioned, at least two x-ray images of the patient and/or one of the parts of his body in the vicinity of a radiation target point are produced from different respective recording angles on a single image recorder;
    c) the x-ray image is spatially localized;
    d) at least one reconstructed image, corresponding to each x-ray image and deriving from a three-dimensional patient scan data set, is produced, the reconstructed images giving the desired image content of the respective x-ray image when the patient is correctly positioned;
    e) the reconstructed images and the x-ray images are superimposed, and a positioning error is determined electronically and/or with computer guidance; and
    f) the position of the patient is corrected by way of the determined positioning error; and
    wherein the x-ray images are produced in defined positions offset with respect to the location at which the patient is pre-positioned and, outside of the irradiating range of the linear accelerator, the reconstructed images being produced with the same offset.

2. The method as set forth in claim 1, wherein the defined offset is compensated for by correcting the position of the patient.

3. The method as set forth in claims 1, wherein the position of the patient is altered by shifting the patient table using markers on at least one of patient and patient table.

4. The method as set forth in claim 1, wherein the position of the patient is corrected by manually guiding the table.

5. The method as set forth in claim 1, wherein the positional error is determined by superimposing the x-ray images and the reconstructed images using image fusion.

6. A method for accurately positioning a patient for radiotherapy and/or radiosurgery, comprising the following steps:
    a) the patient is pre-positioned with respect to a linear accelerator;
    b) after the patient has been pre-positioned, at least two x-ray images of the patient and/or one of the parts of his body in the vicinity of a radiation target point are produced from different respective recording angles on a single image recorder;
    c) the x-ray image is spatially localized;
    d) at least one reconstructed image, corresponding to each x-ray image and deriving from a three-dimensional patient scan data set, is produced, the reconstructed images giving the desired image content of the respective x-ray image when the patient is correctly positioned;
    e) the reconstructed images and the x-ray images are superimposed, and a positioning error is determined electronically and/or with computer guidance; and
    f) the position of the patient is corrected by way of the determined positioning error; and
    wherein the x-ray images are produced at an oblique angle on the single image recorder spatially arranged horizontally, and projected back onto each respectively defined normal plane, the corresponding reconstructed images being likewise produced in these normal planes.

7. The method as set forth in claim 6, wherein the patient is pre-positioned by means of a navigation and tracking system with computer and camera guidance, with the aid of artificial arrangements of markers on the patient and on the devices for treatment.

8. The method as set forth in claim 6, wherein the patient is pre-positioned using markings on the patient's skin, natural landmarks or laser markings.

9. The method as set forth in claim 6, wherein the x-ray images and the reconstructed images are superimposed by way of natural structures present in the x-ray images and the reconstructed images.

10. The method as set forth in claim 9, wherein the x-ray images and the reconstructed images are superimposed by marking them manually and sliding them over one another on a computer display unit.

11. The method as set forth in claim 9, wherein the x-ray images and the reconstructed images are superimposed by automatic, computer-guided image fusion.

12. The method as set forth in claims 6, wherein the x-ray images and the reconstructed images are superimposed by way of artificial structures present in the x-ray images and the reconstructed images.

13. The method as set forth in claims 6, wherein the reconstructed image/s is/are produced as:
Digitally Reconstructed Radiographs (DRRs);
Digitally Composited Radiographs (DCRs);
MIP images,
or as any two-dimensional image reconstruction from a three-dimensional patient scan data set.

14. A method for accurately positioning a patient for radiotherapy and/or radiosurgery, comprising the following steps:
a) the patient is pre-positioned with respect to a linear accelerator;
b) after the patient has been pre-positioned, at least two x-ray images of the patient and/or one of the parts of his body in the vicinity of a radiation target point are produced from different respective recording angles on a single image recorder;
c) the x-ray image is spatially localized;
d) at least one reconstructed image, corresponding to each x-ray image and deriving from a three-dimensional patient scan data set, is produced, the reconstructed images giving the desired image content of the respective x-ray image when the patient is correctly positioned;
e) the reconstructed images and the x-ray images are superimposed, and a positioning error is determined electronically and/or with computer guidance; and
f) the position of the patient is corrected by way of the determined positioning error; and
wherein a multitude of images over a breathing cycle are produced from each angle, each time x-ray image are produced from the different recording angles, the breath-dependent movement of the markings arranged on the patient or in the vicinity of the radiation target being tracked by a navigation and tracking system with computer and camera guidance and referenced with the dynamic shifting of the target point directly or indirectly visible in the images, in order to take into account the breath-dependent shifting of the target point during irradiation.

15. A device for accurately positioning a patient for radiotherapy and/or radiosurgery, comprising:
a) at least two x-ray sources with which x-ray images of the patient and/or one of the parts of his body in the vicinity of the radiation target point may be produced from respectively different recording angles;
b) a means by which the x-ray image may be spatially localized;
c) a means by which at least one reconstructed image, corresponding to each x-ray image and deriving from a three-dimensional patient scan data set, may be produced;
d) a means by which the reconstructed images and the x-ray images are superimposed, the positioning error being determined electronically and/or with computer guidance by way of particular landmarks and/or the intensity gradient or the contours in the two images; and
e) a means by which the position of the patient is corrected with respect to a linear accelerator by way of the determined positioning error, and wherein
f) the device comprises only one image recorder, with which the x-ray images of both x-ray sources are produced, the image recorder being positioned on a support for a movable patient table.

16. The device as set forth in claim 15, wherein the image recorder is an image intensifier or detector.

17. The device as set forth in claim 15, wherein the image recorder is movable vertically together with the patient table and the support, while it is securely arranged horizontally.

18. The device as set forth in claim 15, wherein the two x-ray sources are arranged respectively over a patient table and to the side.

19. The device as set forth in claim 15, wherein the two x-ray sources are arranged respectively beneath a patient table, and to the side, the image recorder being positioned above the patient table.

20. A method for accurately positioning a patient for radiotherapy and/or radiosurgery, comprising the steps of:
pre-positioning the patient with respect to a linear accelerator;
after pre-positioning of the patient, using a single image recorder with an x-ray source to produce at least two x-ray images of at least a portion of the patient in the vicinity of a radiation target point at different respective recording angles;
spatially localizing the x-ray images to obtain respective localized x-ray images;
reconstructing from a three-dimensional patient scan data set reconstructed images respectively corresponding to the localized x-ray images; and
using the reconstructed images and the respective localized x-ray images to determine a positional error between the radiation target point in the reconstructed images and the radiation target point in the localized x-ray images, and
wherein the patient is supported on a table that is shifted relative to the linear accelerator in opposite directions first to position the patient between the single image recorder and a first x-ray source for producing a first one of the x-ray images and then to position the patient between the single image recorder and a second x-ray source for producing a second one of the x-ray images.

21. The method as set forth in claim 20, further comprising adjusting the relative positions of the patient and linear accelerator to compensate for the positional error.

22. A device for accurately positioning a patient relative to a linear accelerator for radiotherapy and/or radiosurgery, comprising:
an image recorder;
first and second x-ray sources cooperative sequentially with the image recorder to produce x-ray images of in the vicinity of a radiation target point at different respective recording angles; and
a patient table for supporting the patient such that at least a portion of the patient can be located in the vicinity of a radiation target point, the table being controllably shiftable in a first direction for positioning at least a portion of the patient between the image recorder and the first x-ray source for producing a first one of the x-ray images and then in a second direction to position the patient between the image recorder and a second x-ray source for producing a second one of the x-ray images.

23. The device as set forth in claim 22, comprising a computer system for spatially localizing the x-ray images to obtain respective localized x-ray images, for reconstructing from a three-dimensional patient scan data set reconstructed images respectively corresponding to the localized x-ray images, and for using the reconstructed images and the respective localized x-ray images to determine a positional error between the radiation target point in the reconstructed image and the radiation target point in the respective localized x-ray image.

* * * * *